US007785892B2

(12) United States Patent
Akahane et al.

(10) Patent No.: US 7,785,892 B2
(45) Date of Patent: Aug. 31, 2010

(54) METHOD OF DETERMINING IRON CONCENTRATION

(75) Inventors: Wataru Akahane, Amagasaki (JP); Haruhisa Ijiri, Amagasaki (JP); Toshiro Hanada, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 31 days.

(21) Appl. No.: 11/918,151

(22) PCT Filed: May 9, 2006

(86) PCT No.: PCT/JP2006/309283

§ 371 (c)(1),
(2), (4) Date: Oct. 10, 2007

(87) PCT Pub. No.: WO2006/121027

PCT Pub. Date: Nov. 16, 2006

(65) Prior Publication Data

US 2009/0068750 A1 Mar. 12, 2009

(30) Foreign Application Priority Data

May 12, 2005 (JP) .............................. 2005-139465

(51) Int. Cl.
*G01N 33/20* (2006.01)
*G01N 33/48* (2006.01)
(52) U.S. Cl. .............................. 436/84; 436/63; 436/73; 436/74; 436/79; 436/164; 436/166

(58) Field of Classification Search .................. 436/63, 436/73, 74, 79, 84, 164, 166; 422/55, 61; 252/408.1
See application file for complete search history.

(56) References Cited

U.S. PATENT DOCUMENTS

| 3,925,020 A | * | 12/1975 | Ogawa et al. ................. 436/57 |
| 4,324,758 A | * | 4/1982 | Eisentraut et al. ............. 422/61 |
| 4,588,695 A |   | 5/1986 | Takano et al. |
| 4,810,656 A | * | 3/1989 | Torelli .......................... 436/74 |
| 5,420,008 A | * | 5/1995 | Nishida et al. ................. 435/4 |
| 6,274,382 B1 | * | 8/2001 | Treiber ......................... 436/74 |

FOREIGN PATENT DOCUMENTS

| JP | 3-56425 | 8/1991 |
| JP | 5-10956 | 1/1993 |
| WO | WO 01/81930 A2 | 11/2001 |

OTHER PUBLICATIONS

Manual of Clinical Laboratory Method ed., Masamitsu Kanehara, rev.32$^{nd}$ ed., 1$^{st}$ issue, p. 579-581, Feb. 20, 2005. Kanchara & Co., Ltd. including English translation of p. 580, line 19 to p. 581, line 7.
Supplementary European Search Report of EP 06746114, issued by the European Patent Office Aug. 28, 2008.

* cited by examiner

*Primary Examiner*—Maureen M Wallenhorst
(74) *Attorney, Agent, or Firm*—Hamre, Schumann, Mueller & Larson, P.C.

(57) ABSTRACT

The present invention discloses a method of measuring iron concentration in a sample. The method includes bringing iron contained in the sample into contact with a metallochromic indicator for iron in the presence of lithium ion and determining the iron concentration based on the degree of resultant coloring. The present disclosure further includes a reagent and a kit using therefor.

9 Claims, No Drawings

METHOD OF DETERMINING IRON CONCENTRATION

TECHNICAL FIELD

The present invention relates to a method of measuring iron concentration in a sample by a direct method using a metallochromic indicator for iron, wherein the method is carried out in the presence of lithium ion.

BACKGROUND ART

Measurement of iron concentration in serum and plasma has been utilized for the diagnosis of anemia, hypo ferric anemia, hepatic cirrhosis and the like, and is one of important measuring items in the field of clinical diagnosis.

As the method of measuring iron concentration, for example, calorimetric analysis using various metallochromic indicators such as, for example, dipyridyl, o-phenanthroline and the like have been employed commonly. From the viewpoints of sensitivity, specificity, solubility and so on, a metallochromic indicator for iron such as bathophenanthroline, 2-nitroso-5-(N-propyl-N-sulfopropylamino)-phenol (nitrosoPSAP), 3-(2-pyridyl)-5,6-bis[2-(5-furylsulphonic acid)]-1,2,4-triadine disodium salt, tripyridyl-triazine, ferrozine and the like has been used more commonly.

Since all of these metallochromic indicators can react only with bivalent iron, it is necessary to use a reducing agent in order to reduce trivalent iron when such metallochromic indicators are used. As a reducing agents for trivalent iron, L-ascorbic acid, thioglycolic acid, hydroxylamine hydrochloride, hydroquinone, hydrosulfite, sodium sulfite, hydrazine sulfate, metabisulfite (pyrosulfite) and the like have been known.

The entire iron atoms in serum exist in a form bound to transferrin, which is a type of serum globulins. Therefore, in order to measure the total concentration of iron in serum, it is necessary to release the iron from transferrin and to generate free iron before conducting measurement of iron concentration. As to a method of releasing the bound iron from transferrin, for example, the International Standard Method in which a protein removal method has been incorporated (Manual of Clinical Laboratory Method, ed. by Masamitsu Kanehara, rev. 32nd ed., p. 579, published in Feb. 20, 2005 by Kanehara & Co., Ltd.) and the Matsubara's modified method which has been emphasized as basic data during the process for establishing the International Standard Method (Manual of Clinical Laboratory Method, ed. by Masamitsu Kanehara, rev. 32nd ed., $1^{st}$ issue, p. 580-581, published in Feb. 20, 2005 by Kanehara & Co., Ltd.) have been known. According to these methods, after removing protein in a sample to be measured for iron concentration, a metallochromic indicator for iron is added to the sample to measure absorbance, and thus the total concentration of iron in a sample can be measured.

By the way, in recent years, in association with the development of automated analyzers, clinical laboratory test is now being performed commonly using an automated analyzer. Use of such an automated analyzer is economical because volumes of specimen and reagent solution to be collected for the measurement can be made small, and has an advantage in capability of processing a large number of specimens at the same time. Accordingly, it is desired that the measurement of concentration of iron in serum or the like is also performed using an automated analyzer. However, since the International Standard Method and the Matsubara's modified method require a protein removal treatment prior to performing the measurement of iron, there is a problem that it is difficult to apply these methods to the measurement using an automated analyzer.

On the other hand, there is a method of measuring iron concentration called "direct calorimetric method" (hereinafter referred to as "direct method"), in which measurement of iron concentration is performed by adding a reducing agent and a metallochromic indicator directly to a sample (for example, non-patent reference 1: Manual of Clinical Laboratory Method, ed. by Masamitsu Kanehara, rev. 32nd ed., $1^{st}$ issue, p. 579, published in Feb. 20, 2005 by Kanehara & Co., Ltd.). Since this method does not require the protein removal treatment in contrast to the above-described International Standard Method and the like, it can be applied to the system using an automated analyzer. Therefore, in the field of clinical laboratory test, the direct method of measuring iron concentration using an automated analyzer has been in widespread use.

However, there still remains a problem that the measured value obtained by the direct method using an automated analyzer is lower as compared to that obtained by the International Standard Method. In the International Standard Method, iron in a sample can be released completely (100%) from transferrin because sample is subjected to the protein removal treatment, while iron cannot be released completely from transferrin in the direct method using an automated analyzer, and it has been reported that percentage of the released iron (degree of release) is in a range from about 93 to 95% (the 51st plenary meeting of the Japanese Society of Laboratory Medicine, presentation No. 0-76, 2004), and this has been considered to be one of causes, which give rise to such problem as described above.

Therefore, under the current situation, establishment of a method of measuring iron concentration, which can provide the same level of measured value as that obtained by the International Standard Method and can be applied to the automated analyzer system, has been desired.

Non-patent Document 1: Manual of Clinical Laboratory Method, ed. by Masamitsu Kanehara, rev. 32nd ed., $1^{st}$ issue, p. 579, published in Feb. 20, 2005 by Kanehara & Co., Ltd.

DISCLOSURE OF THE INVENTION

Problems to be Solved by the Invention

The present invention has been made in view of the above situation, and has an object to provide a method of measuring iron concentration by a direct method, which can provide an equivalent measured value to that obtained by the International Standard Method, and a reagent and a kit to be used in the method.

Means for Solving Problems

The present invention has been made to achieve the above-described object, and comprises the following aspects:

(1) A method of measuring iron concentration in a sample, characterized by bringing the iron contained in the sample into contact with a metallochromic indicator for iron in the presence of lithium ion and determining the iron concentration based on the degree of resultant coloring, (2) A reagent for measuring iron concentration, comprising a metallochromic indicator for iron and lithium ion, and (3) A kit for measuring iron concentration, comprising a reagent containing a metallochromic indicator for iron and lithium ion as a constituent reagent.

Namely, the present inventors have intensively studied a way to solve the above-described problem, and found that by carrying out the measurement of iron concentration by the direct method in the presence of lithium ion, release of iron from transferrin is promoted and the reaction of iron with a metallochromic indicator for iron proceeds stoichiometrically, and thus accomplished the present invention. Up to now, as the metallochromic indicator for iron, sodium salts such as sodium bathophenanthrolinesulfonate, 3-(2-pyridyl)-5,6-bis[2-(5-furylsulphonic acid)]-1,2,4-triadine disodium salt and the like have been used commonly, but such an effect as provided by the present invention has not been obtained by these sodium salts. Also, any example practically using a lithium salt as a salt of these metallochromic indicators for iron has not been found. Therefore, it was unexpected finding that such an effect as described above can be obtained when an ion derived from lithium which belongs to the same alkali metal element as sodium is present.

Effects of the Invention

By performing the method of measuring iron concentration of the present invention, the conventional problem that the measured value is lower as compared with that obtained by the International Standard Method is solved; a complicated procedures such as protein removal treatment or the like are not required; the measurement of iron concentration with an automated analyzer is enabled; and more accurate measurement becomes possible, since the measured value obtained by the present method is very close to that obtained by the standard addition method according to the International Standard Method,

BEST MODE FOR CARRYING OUT THE INVENTION

The method of measuring iron concentration according to the present invention is "a method of measuring iron concentration in a sample, characterized by bringing the iron contained in the sample into contact with a metallochromic indicator for iron in the presence of lithium ion and determining the iron concentration based on the degree of resultant coloring".

The metallochromic indicator for iron to be used in the present invention may be a metallochromic indicator for bivalent iron, which has a specific absorption by binding to iron. For example, the metallochromic indicators for iron used in the direct method of measuring iron concentration well known per se can be used.

Specific example of the metallochromic indicator for iron includes, for example, bathophenanthrolinesulfonic acid or salts thereof, 2-nitroso-5-(N-propyl-N-sulfopropylamino)-phenol, 3-(2-pyridyl)-5,6-bis[2-(5-furylsulphonic acid)]-1,2,4-triadine or salts thereof, and the like.

The salts of bathophenanthrolinesulfonic acid or 3-(2-pyridyl)-5,6-bis[2-(5-furylsulphonic acid)]-1,2,4-triadine include, for example, salts with alkaline metal such as sodium, potassium, lithium or the like.

An amount of the metallochromic indicator for iron according to the present invention is not particularly limited, and may be measured depending on the properties of the metallochromic indicator for iron.

For example, when bathophenanthrolinesulfonic acid or a salt thereof is used, the concentration thereof in the reagent solution is in a range from about 0.5 to 5 mM, preferably from about 1 to 2 mM, and a final concentration in the reaction solution is in a range from about 0.1 to 1 mM, preferably from about 0.2 to 0.5 mM.

When 2-nitroso-5-(N-propyl-N-sulfopropylamino)-phenol is used, the concentration thereof in the reagent solution is in a range from about 0.2 to 1 mM, preferably from about 0.3 to 0.6 mM, and a final concentration in the reaction solution is in a range from about 0.06 to 0.4 mM, preferably from about 0.1 to 0.2 mM.

When 3-(2-pyridyl)-5,6-bis[2-(5-furylsulphonic acid)]-1,2,4-triadine or a salt thereof is used, the concentration in the reagent solution is in a range from about 1 to 5 mg/mL, preferably from about 1 to 3 mg/mL, and a final concentration in the reaction solution is in a range from about 0.2 to 1 mg/mL, preferably from about 0.3 to 0.7 mg/mL.

The concentration of lithium ion according to the present invention in the reaction solution is not particularly limited, and the amount thereof may also be determined depending on the type of the metallochromic indicator for iron to be used in the same measurement system. However, the concentration in the reagent solution is, as lithium ion, in a range from about 0.1 to 100 mM, preferably from about 1 to 100 mM, and a final concentration in the reaction solution is in a range from about 0.05 to 100 mM, preferably from about 0.5 to 100 mM.

Since the measuring method according to the present invention uses a metallochromic indicator for bivalent iron, trivalent iron binding to transferrin in the sample has to be released from transferrin and reduced to bivalent iron. As a reducing agent for trivalent iron to be used for this purpose, any kind of reducing agent usually used in this field including ascorbic acid, glutathione, sodium pyrosulfite, thioglycolic acid, hydroxylamine hydrochloride, thiol compounds, and the like can be used. Among them, ascorbic acid is used commonly.

The amount of the reducing agent cannot be categorically specified, because it varies depending on the type of reducing agent and the metallochromic indicator for iron to be used, pH in use, and also necessary amount thereof increases with rise of pH, but may be selected from the range usually used in this field. The concentration of the reducing agent in the reagent solution is in a range from about 0.0006 to 400 mM, preferably from about 10 to 150 mM, and a final concentration in the reaction solution is in a range from about 0.0005 to 300 mM, preferably from about 10 to 100 mM.

To perform the method of measuring iron concentration of the present invention, the method may be carried out according to the measuring conditions (for example, reaction time, measuring wavelength, etc.) and the method of operating the direct method well known per se usually performed in the field of clinical laboratory tests, except that the measurement is carried out using a metallochromic indicator for iron by the direct method well known per se in the presence of lithium ion.

When the method of measuring iron concentration is performed by the direct method, method of making lithium ion be present is not particularly limited so long as a solution containing a sample, a reducing agent, lithium ion and a metallochromic indicator for iron can be finally obtained. However, it is preferable that lithium ion is added after the sample is treated with a reducing agent or simultaneously together with a reducing agent to the sample. In addition, the metallochromic indicator for iron is preferably added after addition of lithium ion or simultaneously together with lithium ion, but not limited thereto. In this regard, however, it is undesirable to add the metallochromic indicator for iron to the sample before lithium ion is added.

In addition, as to the method of making lithium ion be present in the measurement system of the direct method, use of lithium ion in the form of a salt thereof is usually the simplest way, but is not particularly limited thereto. Type of the salt to be used in this method is not particularly limited, so long as the salt does not inhibit stability of the reagent and the like present in the solution or does not inhibit color development of the metallochromic indicator for iron, and includes, for example, salts with inorganic acids such as sulfuric acid, nitric acid and the like; salts with halogen atom (halides) such as chlorine, bromine, iodine and the like; salts with organic acids such as acetic acid, citric acid, gluconic acid, propionic acid, pantothenic acid and the like; salts with the above-described metallochromic indicator for iron; and the like.

When the method of measuring iron concentration by the direct method is performed, specific method of making lithium ion be present includes, for example, the following methods:

(1) A method, in which a solution of a reducing agent, a solution containing lithium ion, and a solution of a metallochromic indicator for iron are prepared in advance, and these solutions are added to the sample in the order of the solution of a reducing agent, the solution containing lithium ion and then the solution of a metallochromic indicator for iron;

(2) A method, in which a solution containing a reducing agent and lithium ion and a solution of a metallochromic indicator for iron are prepared, and then these solutions are added to the sample in the order of the solution containing a reducing agent and lithium ion and then the solution of a metallochromic indicator for iron;

(3) A method, in which a solution of a reducing agent and a solution containing lithium ion and a metallochromic indicator for iron are prepared, and then these solutions are added to the sample in the order of the solution of a reducing agent and the solution containing lithium ion and metallochromic indicator for iron; and (4) A method, in which a solution containing a reducing agent, lithium ion and a metallochromic indicator for iron is prepared, and then the solution is added to the sample allowing these components to react at the same time.

Among the methods described above, in view of operational efficiency and the like, the method (2) is common and preferable.

Also, commercial products for measuring iron concentration using a metallochromic indicator for iron, which is usually used in the clinical laboratory test, may be used by adding lithium ion to any one of constituent reagents of the commercial product so that the above-described condition is produced.

As to the solution for dissolving a metallochromic indicator for iron, lithium ion and a reducing agent, since the measurement of iron concentration is desirably carried out at the optimal pH range for the metallochromic indicator for iron, a buffer solution is preferable.

Preferable pH range in the measurement according to the measurement method of the present invention is pH 1 to 7, more preferably pH 2 to 6. As a buffering agent composing the buffer solution to be used for adjusting pH value within the range described above, any buffering agent usually used in this field can be used. Specifically, it includes, for example, glycine, acetic acid, citric acid, tartaric acid and the like.

Further, besides these reagents, it goes without saying that a surface active agent, various types of antiseptic agents, a stabilizer, an activating agent, an agent for avoiding side effect of coexisting substances and substances usually used for the clinical diagnostics may be present. Although range of the concentration, etc. of these reagents and the like may be selected as appropriate from the range of the concentration, etc. usually used in the measurement method well known per se, it is desirable to select the range that gives high stability and does not inhibit color development of the metallochromic indicator for iron in the optimal pH range of the metallochromic indicator for iron to be used in the method of measuring iron concentration of the present invention.

As to the surface active agent to be used for the measurement method according to the present invention, any of non-ionic surface active agent, cationic surface active agent, anionic surface active agent or amphoteric surface active agent can be used, so long as it does not inhibit color development of the metallochromic indicator for iron. The surface active agent may be used by selecting as appropriate depending on properties of color development of the metallochromic indicator for iron to be used.

For example, the concentration of the above-described surface active agent may be selected as appropriate from the range usually used in this field. The concentration in the reagent solution is usually around 0.0001 to 10% (w/v), preferably around 0.001 to 5% (w/v), and a final concentration in the reaction solution is usually around 0.001 to 10% (w/v), and preferably around 0.01 to 5% (w/v).

After allowing the metallochromic indicator for iron and lithium ion to react with the sample, measurement of color development produced by the action of the metallochromic indicator for iron may be carried out according to the direct method well known per se. As to other reagents, an automated analyzer, a spectrophotometer and the like to be used in the measurement, any one usually used in this field can be used without exceptions. In addition, it goes without saying that absorbance change can be measured by means of dual wavelength photometry employing main wavelength and sub-wavelength.

In this regards, wavelength for the measurement of absorbance may be selected as appropriate depending on the type of metallochromic indicator for iron to be used. When bathophenanthrolinesulfonic acid or a salt thereof is used as the metallochromic indicator for iron and measurement is conducted using dual wavelength, the measurement is preferably carried out at around 540 nm for the main wavelength and at around 600 nm for the sub-wavelength.

Sample to be used in the method of the present invention includes, for example, blood components such as serum, plasma, and the like.

The method of measuring iron concentration of the present invention will be specifically explained according to the above-described method (2) (a method, in which a solution containing a reducing agent and lithium ion and a solution of a metallochromic indicator for iron are prepared, and then these solutions are added to the sample in the order of the solution containing a reducing agent and lithium ion and then the solution of a metallochromic indicator for iron) as an example, as follows.

Firstly, a sample to be measured for iron concentration such as blood, serum, plasma, and the like is mixed with a first reagent solution (pH 2-6) containing a reducing agent, lithium ion, a buffering agent, and if needed, a surface active agent and the like, and allowed to react generally at 10 to 50° C., preferably at 20 to 40° C., for generally 2 to 10 minutes, preferably about 5 minutes. After that, the obtained reaction solution is mixed with a second reagent solution (pH 2-10) containing a metallochromic indicator for iron, a buffering agent, and if needed, a buffering agent, an antiseptic agent, a surface active agent and the like, and allowed to react generally at 10 to 50° C., preferably at 20 to 40° C., for generally 2 to 15 minutes, preferably about 10 minutes. The color developed by the action of the metallochromic indicator for iron is measured as an absorbance. Iron concentration in the sample is determined by applying the measured value to the calibration curve showing the relationship between iron concentration and absorbance, which is previously obtained by performing the same measurement using standard iron solutions with known concentrations.

It is obvious that the measurement of iron concentration as described above may be carried out by manual means, and it goes without saying that the measurement can also be performed using an automated analyzer, because the method of the present invention can be applied to the measurement system using an automated analyzer. In this connection, combination of the reagents in the measurement by manual means or using an automated analyzer is not particularly limited, and may be selected in accordance with the circumstance, other factors, and the like of the automated analyzer to be applied.

The reagent for the measuring of iron concentration according to the present invention comprises a metallochromic indicator for iron and lithium ion, and preferable embodiment, specific example, concentration and the like thereof are as described above.

The kit for the measuring iron concentration of the present invention may be any one comprising a reagent containing a metallochromic indicator for iron and lithium ion as a constituent reagent. Preferable embodiment, specific example, concentration in use and the like of each component are as described above.

In addition, in each reagent of the kit, for example, a buffering agent, an antiseptic agent, a surface active agent, a stabilizer and the like usually used in this field, may be contained within the ranges usually used in this field. Further, the kit may contain, if needed, a standard iron solution in combination.

In addition, when the kit is composed of a plurality of reagent solutions, the reagents necessary for the measurement of the analyte have to be contained in each reagent solution, but these reagents may be distributed properly to any one of reagent solutions so that the reaction for the measurement of the analyte starts when each reagent solution is mixed together. Concentrations in use of the reagents constituting these reagent solutions may be selected as appropriate from the ranges usually used in this field.

Specific embodiment of the kit of the present invention includes, for example, the following compositions:

(1) One comprising a first reagent solution containing a reducing agent and a second reagent solution containing a metallochromic indicator for iron, and lithium ion is contained at least one of the first reagent solution or the second reagent solution.

(2) One comprising a reagent solution as a constituent reagent containing a reducing agent, lithium ion and a metallochromic indicator for iron.

Hereinafter, the present invention will be further explained in detail by referring to the following Examples and Comparative Examples, but the scope of the present invention should not be limited thereto.

EXAMPLES

Reference Example 1

Iron concentrations in the same serum samples 1 to 5 were measured by the International Standard Method, the standard addition method according to the International Standard Method (In the International Standard Method, sample volume is lost due to the protein removal treatment. In this method, for the purpose of its correction, measurements are carried out using samples added with 3 different concentrations of iron, and the iron concentration in the sample is obtained from the intersecting point on the X-axis of the regression formula.) and the conventional direct method using an automated analyzer, and measured value for each sample was compared with each other.

(1) International Standard Method

According to the method described in the Manual of Clinical Laboratory Method, ed. by Masamitsu Kanehara, rev. 32nd ed., $1^{st}$ issue, p. 580, published in Feb. 20, 2005 by Kanehara & Co., Ltd., the measurement was carried out as follows.

(Preparation of Reagents)

Protein removing reagent: Trichloroacetic acid (special grade) 98 g was dissolved in 600 mL of water, then 30 mL of thioglycolic acid and 83 mL of hydrochloric acid (special grade) were added to the solution and mixed. Subsequently, the solution was made up to 1000 mL with water and stored in a brown colored bottle.

Color reagent: Bathophenanthrolinesulfonic acid (Dotite reagent) 250 mg was added to 1000 mL of 1.5 M aqueous solution of sodium acetate (special grade) to be dissolved therein.

Standard iron solution (200 µg/dL): Standard iron solution (Fe 1000) (produced by Wako Pure Chemical Industries, Ltd.) 1 mL was diluted to 100 mL with water (1 mg/dL). This solution was further diluted by 5-fold with water for use.

(Measurement of Iron Concentration in Serum)

1) Two mL each of serum samples 1 to 5 was taken in a container, and 2 mL of the protein removing reagent was added thereto and mixed sufficiently using a mixer. After that, the mixture was heated at 56° C. for 15 minutes, and then mixed again and centrifuged.

2) Supernatant 2.0 mL was obtained, and 2.0 mL of the color reagent was added thereto and left for 10 minutes.

3) For water (for blank test) and the standard iron solution, the same procedures as in the above 1) and 2) for the serum sample were carried out (except that centrifugation was not conducted).

4) Absorbance at 535 nm was measured for each of the serum sample, the standard iron solution and the blank test sample using water as a control, and the measured values were expressed as $E_a$, $E_s$ and $E_b$, respectively. The iron concentrations in serum in each sample was measured by the following equation:

$$\text{Iron concentration in serum} = 200 \times (E_a - E_b)/(E_s - E_b) \text{ µg/dL.}$$

The results are shown in Table 1.

(2) Standard Addition Method According to the International Standard Method

In the International Standard Method, sample volume is lost due to the protein removal treatment. In this method, for the purpose of its correction, measurements are carried out using samples added with 3 different concentrations of iron, and the iron concentration in the sample is obtained from the intersecting point on the X-axis of the regression formula.

(Preparation of Reagents and Sample Solutions)

Two mL of each of the serum samples 1 to 5 same as used in the International Standard Method was taken in 4 containers, three of them were added with the standard iron solution so that iron concentration becomes 50 µg/dL, 100 µg/dL and 150 µg/dL, respectively. These three samples and another sample, which was not added with the standard iron solution, were used as the sample solutions.

The reagents used were the same ones as used in the International Standard Method described in the above (1).

(Measurement of Iron Concentration in Serum)

Measurement of absorbance was carried out for the sample solutions prepared as described above by the same procedures as used in the International Standard Method described in the above (1).

A graph showing the relationship between the absorbance and the obtained iron concentration was prepared, and the iron concentration in the sample was measured from the distance between the intersecting point on the X-axis of the regression formula and the original point.

The results are shown together in Table 1.

(3) Measuring Method by Conventional Direct Method Using an Automated Analyzer

Iron concentrations in the serum samples 1 to 5 were measured using commercially available kits for measuring iron concentration by the direct method (produced by Company A, B and C, and designated as kit A, kit B and kit C, respectively) each having following composition, according to the standard procedures described in the instruction of each kit, and setting each measurement parameter as follows.

The results are shown together in Table 1.

In this connection, the measurements were carried out using Hitachi Autoanalyzer Model 7170S (produced by Hitachi, Ltd.), and the iron concentration was determined by applying the absorbance values to the calibration curve showing the relationship between iron concentration and absorbance, which was previously obtained by performing the same measurements using the samples with known concentrations instead of the serum sample.

(Kit A)

(R-1) Buffer solution: 400 mM glycine buffer (pH 3.5) containing 40 mM ascorbic acid and a surface active agent.

(R-2) Color reagent: 40 mM glycine buffer (pH 3.0) containing 1.86 mM sodium bathophenanthrolinesulfonate and a surface active agent.

Measurement method; 2 point end [16]-[34],
Sample volume; 12 µL,
R-1; 160 µL,
R-2; 40 µL,
Measurement wavelength; 600/546 nm,
Measurement temperature; 37° C.,
Concentration of standard iron solution; 200 µg/dL.

(Kit B)

(R-1) Reducing agent solution: a solution containing L-ascorbic acid.

(R-2) Color reagent: a solution containing 0.45 mM 2-nitroso-5-(N-propyl-N-sulfopropylamino)-phenol.

Measurement method; 2 point end [16]-[34],
Sample volume; 15 µL,
R-1; 150 µL,
R-2; 60 µL,
Measurement wavelength; 750/600 nm,
Measurement temperature; 37° C.,
Concentration of standard iron solution; 200 µg/dL.

(Kit C)

(R-1) Buffer solution: composition unknown.

(R-2) Color reagent: a solution containing 2.47 mg/mL of 3-(2-pyridyl)-5,6-bis[2-(5-furylsulphonic acid)]-1,2,4-triadine disodium salt and others.

Measurement method; 2 point end [16]-[34],
Sample volume; 12 µL,
R-1; 180 µL,
R-2; 45 µL,
Measurement wavelength; 700/600 nm,
Measurement temperature; 37° C.,
Concentration of standard iron solution; 200 µg/dL.

The results are shown in Table 1 below.

In Table 1, assuming the measured value obtained by the standard addition method according to the International Standard Method to be 100, percentages of the measured values obtained by the International Standard Method or the direct method using kit A, B or C are shown in parentheses under each mean value, respectively.

TABLE 1

| | Iron concentration in serum (µg/dL) | | | | |
|---|---|---|---|---|---|
| | International Standard Method | Standard Addition Method according to the International Standard Method | A | B | C |
| Serum 1 | 126 | 120 | 118 | 114 | 115 |
| Serum 2 | 148 | 143 | 139 | 135 | 133 |
| Serum 3 | 98 | 95 | 93 | 89 | 87 |
| Serum 4 | 128 | 122 | 119 | 115 | 114 |
| Serum 5 | 187 | 179 | 175 | 169 | 170 |
| Mean | 137.4 (104.2%) | 131.8 (100%) | 128.8 (97.7%) | 124.4 (94.4%) | 123.8 (93.9%) |

As is clear from Table 1, all of the measured values obtained by the measurement based on the conventional direct method are lower as compared with those obtained by the International Standard Method and the standard addition method.

Example 1

Preparation of Reagent Solutions (R-1) Buffer Solution 400 mM glycine buffer (pH 3.5) containing 10 mM lithium chloride, sodium chloride, potassium chloride or cesium chloride (10 mM as alkaline metal ion), 40 mM ascorbic acid and a surface active agent.

(R-2) Color Reagent Solution 40 mM glycine buffer (pH 3.0) containing 1.86 mM sodium bathophenanthrolinesulfonate and a surface active agent.

(Measurement of Iron Concentration in Serum)

Measurement was performed in the serum samples 6 to 10 using the above-described reagent solutions and Hitachi Autoanalyzer Model 7170S (produced by Hitachi, Ltd.).

(Measurement Conditions)

Iron concentration in each serum sample was measured by setting measurement parameters as follows;

Measurement method; 2 point end [16]-[34],
Sample volume; 12 µL,
R-1; 160 µL,
R-2; 40 µL,
Measurement wavelength; 600/546 nm,
Measurement temperature; 37° C.,
Concentration of the standard iron solution; 200 µg/dL.

Iron concentrations were determined by applying the absorbance values to the calibration curve showing the relationship between iron concentration and absorbance, which was previously obtained by performing the same measurements using the samples with known concentration instead of the serum sample.

In this connection, concentration of alkaline metal ion in the measurement was about 7.5 mM.

(Results)

The results are shown in Table 2.

As a control, the measurement by the standard addition method according to the International Standard Method as described in Reference Example 1 was carried out using the same serum samples. The results are shown together in Table 2.

In Table 2, percentages of the measured values obtained by the direct method in the presence of various alkaline metal ions when the measured value obtained by the standard addition method according to the International Standard Method assumed to be 100 are shown in parentheses under each mean value, respectively.

In addition, the difference between "percentage (%) of the measured value obtained by the direct method in the presence of various alkaline metal ions, when the measured value obtained by the standard addition method according to the International Standard Method is assumed to be 100" and the measured value obtained by the standard addition method according to the International Standard Method (100%) was shown together as "difference between the International Standard Method and the standard addition method" in Table 2.

bound to a metallochromic indicator for iron to develop the color only in the presence of lithium ion.

Example 2

Measurement of iron concentrations in the serum samples 11 to 15 was carried out by the same method as described in Example 1 using the same reagents prepared as in Example 1, except that lithium chloride was added to "(R-1) buffer solution" so that the concentration thereof became 0.1 mM, 1 mM, 10 mM or 100 mM (a final concentration of lithium ion in the measurement was 0.075 mM, 0.75 mM, 7.5 mM or 75 mM, respectively).

The results are shown in Table 3.

As a control, the measurement by the standard addition method according to the International Standard Method as

TABLE 2

| | Iron concentration in serum (μg/dL) | | | | | |
|---|---|---|---|---|---|---|
| | Standard addition Method according to the International Standard Method | Alkaline metal ion | | | | |
| | | No addition | Li | Na | K | Ce |
| Serum 6 | 127 | 123 | 126 | 124 | 123 | 125 |
| Serum 7 | 152 | 147 | 153 | 147 | 147 | 149 |
| Serum 8 | 113 | 111 | 113 | 112 | 112 | 112 |
| Serum 9 | 178 | 173 | 176 | 173 | 175 | 175 |
| Serum 10 | 88 | 85 | 87 | 86 | 85 | 86 |
| Mean | 131.6 | 127.8 | 131.0 | 128.4 | 128.4 | 129.4 |
| | (100%) | (97.1%) | (99.5%) | (97.6%) | (97.6%) | (98.3%) |
| Difference between the international standard method and the standard addition method | | 2.9% | 0.5% | 2.4% | 2.4% | 1.7% |

As is clear from Table 2, when the direct method is carried out in the presence of an alkaline metal ion such as sodium, potassium and cesium, the measured values were lower than those obtained by the standard addition method according to the International Standard Method. On the contrary, only when the same direct method is carried out in the presence of lithium ion, the measured values were close to those obtained by the standard addition method according to the International Standard Method, and found to be able to achieve the object of the present invention. It is supposed that when iron atoms are released from transferrin, all of free irons can be described in Reference Example 1 was carried out using the same serum samples. The results are shown together in Table 3.

In Table 3, percentages of the measured values obtained by the direct method in the presence of various concentrations of lithium chloride when the measured value obtained by the standard addition method according to the International Standard Method to be 100 are shown in parentheses under each mean value, respectively.

TABLE 3

| | Iron concentration in serum (μg/dL) | | | | | |
|---|---|---|---|---|---|---|
| | Standard addition Method according to the International Standard Method | Lithium ion concentration at the measurement time (mM) | | | | |
| | | 0 | 0.075 | 0.75 | 7.5 | 75 |
| Serum 11 | 138 | 132 | 136 | 137 | 138 | 138 |
| Serum 12 | 115 | 112 | 114 | 116 | 115 | 116 |
| Serum 13 | 174 | 169 | 171 | 175 | 173 | 175 |
| Serum 14 | 138 | 134 | 135 | 137 | 138 | 137 |
| Serum 15 | 92 | 90 | 90 | 93 | 92 | 93 |
| Mean | 131.4 | 127.4 | 129.2 | 131.6 | 131.2 | 131.8 |
| | (100%) | (97.0%) | (98.3%) | (100.2%) | (99.8%) | (100.3%) |

As is clear from Table 3, the measurement of iron concentration can be performed more accurately by the presence of lithium ion. In particular, when concentration of lithium ion present in the measurement is 0.075 mM or more, preferably within a range from 0.075 to 75 mM, no difference was observed among the measured values, and the measured values were also well agree with the value obtained by the standard addition method according to the International Standard Method.

Example 3

Measurement of iron concentrations in the serum samples 16 to 20 were carried out by the same method as in Reference Example 1, except that in "(3) Measuring method by conventional direct method using an automated analyzer" in Reference Example 1, the buffer solution or the reducing agent solution of each kit, in which lithium chloride was added so that the concentration thereof became 10 mM (a final concentration of lithium ion in the measurement was 7.5 mM for kit A and C, and 6.7 mM for kit B), was used as "(R-1) buffer solution". The results are shown as "Added" in Table 4.

Also, measurement of iron concentrations in serum in the same serum sample was carried out by "(3) Measurement method by conventional direct method using an automated analyzer" in Reference Example 1. The results are shown together as "Not added" in Table 4.

Further, as a control, the measurement by the standard addition method according to the International Standard Method as described in Reference Example 1 was carried out using the same serum samples. The results are shown together in Table 4.

In this connection, in Table 4, percentages of the measured values obtained in the presence or absence of lithium chloride (lithium ion) when the measured value obtained by the standard addition method according to the International Standard Method to be 100 are shown in parentheses under each mean value, respectively. In addition, percentages of the measured values obtained in the presence of lithium chloride using the same kits when the measured value obtained in the absence of lithium chloride to be 100 are also shown together as "Relative to not added" in Table 4.

same procedures in the absence of lithium chloride, and further, came close to the measured value obtained by the standard addition method according to the International Standard Method.

INDUSTRIAL APPLICABILITY

The present invention provides a method of measuring iron concentration by the direct method, which can provide an equivalent measured value to the International Standard Method, a reagent and a kit to be used in the method.

By performing the method of measuring iron concentration of the present invention, the conventional problem that measured value is lower as compared with that obtained by the International Standard Method is solved; a complicated procedures such as protein removal treatment or the like are not required; the measurement of iron concentration with an automated analyzer is enabled; and more accurate measurement becomes possible, since the measured value obtained by the present method is very close to that obtained by the standard addition method according to the International Standard Method.

What is claimed is:

1. A method of screening a plurality of subjects for possibility of a disorder reflected at least in part by abnormal iron concentrations by measuring iron concentration in a sample taken from each of the subjects, each of the samples being a blood component, comprising:
    bringing iron contained in each of the samples into contact with a metallochromic indicator for iron in the presence of 0.05 to 100 mM of lithium ion;
    determining the iron concentration based on the degree of resultant coloring; and
    determining the possible presence of the disorder based at least in part on the iron concentration.

2. A method according to claim 1, wherein the metallochromic indicator for iron is bathophenanthrolinesulfonic acid or a salt thereof, 2-nitroso-5-(N-propyl-N-sulfopropylamino)-phenol, or 3-(2-pyridyl)-5,6-bis[2-(5-furylsulphonic acid)]-1,2,4-triazine or a salt thereof.

TABLE 4

| | Standard addition Method according to the International Standard Method | A | | B | | C | |
|---|---|---|---|---|---|---|---|
| | | Not added | Added | Not added | Added | Not added | Added |
| Serum 16 | 138 | 132 | 138 | 128 | 129 | 128 | 130 |
| Serum 17 | 115 | 112 | 115 | 109 | 111 | 110 | 111 |
| Serum 18 | 174 | 169 | 173 | 162 | 164 | 161 | 163 |
| Serum 19 | 138 | 134 | 138 | 129 | 130 | 128 | 130 |
| Serum 20 | 92 | 90 | 92 | 86 | 97 | 85 | 88 |
| Mean | 131.4 | 127.4 | 131.2 | 122.8 | 124.2 | 122.4 | 124.4 |
| | (100%) | (97.0%) | (99.8%) | (93.5%) | (94.5%) | (93.2%) | (94.7%) |
| Relative to "Not added" | | 100% | 103.0% | 100% | 101.1% | 100% | 101.6% |

As is clear from Table 4, although the degree of effect varies depending on the type of metallochromic indicator for iron, the measured values obtained by the direct method using the kits for measuring iron concentration were higher when the measurement was carried out in the presence of lithium chloride (lithium ion) as compared with those obtained by the 3. A method according to claim 1, wherein the lithium ion is derived from a lithium salt.

4. A method according to claim 3, wherein the iron contained in the sample is reduced to bivalent by contacting a reducing agent with the iron contained in the sample before contacting the metallochromic indicator with the iron contained in the sample, or by contacting simultaneously the reducing agent and the metallochromic indicator with the iron contained in the sample.

5. A method according to claim 1, wherein the metallochromic indicator for iron is bathophenanthrolinesulfonic acid or a salt thereof.

6. A method according to claim 5, wherein the iron contained in the sample is reduced to bivalent by contacting a reducing agent with the iron contained in the sample before contacting the metallochromic indicator with the iron contained in the sample, or by contacting simultaneously the reducing agent and the metallochromic indicator with the iron contained in the sample.

7. A method according to claim 1, wherein the iron contained in the sample is reduced to bivalent by contacting a reducing agent with the iron contained in the sample before contacting the metallochromic indicator with the iron contained in the sample, or by contacting simultaneously the reducing agent and the metallochromic indicator with the iron contained in the sample.

8. A method according to claim 1, wherein the blood component is serum or plasma.

9. The method of claim 1, wherein the method of measuring iron concentration in the blood component is carried out using an automated analyzer.

* * * * *